United States Patent
Oh et al.

(10) Patent No.: US 12,426,793 B2
(45) Date of Patent: Sep. 30, 2025

(54) PPG SENSOR, ELECTRONIC DEVICE COMPRISING SAME, AND CONTROL METHOD THEREOF

(71) Applicant: SAMSUNG ELECTRONICS CO., LTD., Suwon-si (KR)

(72) Inventors: Youngjae Oh, Suwon-si (KR); Jinhong Min, Suwon-si (KR); Hyoungseon Choi, Suwon-si (KR); Seongje Cho, Suwon-si (KR); Chulho Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 653 days.

(21) Appl. No.: 17/289,504

(22) PCT Filed: Oct. 4, 2019

(86) PCT No.: PCT/KR2019/013019
§ 371 (c)(1),
(2) Date: Apr. 28, 2021

(87) PCT Pub. No.: WO2020/130303
PCT Pub. Date: Jun. 25, 2020

(65) Prior Publication Data
US 2021/0386306 A1  Dec. 16, 2021

(30) Foreign Application Priority Data
Dec. 17, 2018 (KR) .......... 10-2018-0163119

(51) Int. Cl.
*A61B 5/024* (2006.01)
*A61B 5/00* (2006.01)

(52) U.S. Cl.
CPC ........ *A61B 5/02416* (2013.01); *A61B 5/6844* (2013.01); *A61B 5/742* (2013.01)

(58) Field of Classification Search
None
See application file for complete search history.

(56) References Cited

U.S. PATENT DOCUMENTS 6,731,967 B1 * 5/2004 Turcott ............... A61B 5/0261
                                                    600/475
7,369,690 B2    5/2008 Joo et al.
(Continued)

FOREIGN PATENT DOCUMENTS

GB    2528055 A  *  1/2016  ......... A61B 5/02427
JP    3868281       1/2007
(Continued)

OTHER PUBLICATIONS

Swisher et al., "Impedance sensing device enables early detection of pressure ulcers in vivo", Nature Communications, pp. 1-10, Mar. 2015. (Year: 2015).*
(Continued)

*Primary Examiner* — Katherine L Fernandez
(74) *Attorney, Agent, or Firm* — Nixon & Vanderhye, P.C.

(57) ABSTRACT

An electronic device is provided. The electronic device according to an embodiment includes a Photoplethysmography (PPG) sensor including a light source, a detector and a transparent electrode window and a processor configured to, based on determining that a user is in contact with the PPG sensor based on a value sensed by the transparent electrode window, activate the detector, and determine whether a contact between the PPG sensor and the user is poor based on an illuminance value sensed by the detector.

8 Claims, 13 Drawing Sheets

(56) References Cited

U.S. PATENT DOCUMENTS

| | | | |
|---|---|---|---|
| 10,051,177 B2 | 8/2018 | Kim et al. | |
| 10,191,455 B2 | 1/2019 | Shim et al. | |
| 10,758,134 B2 | 9/2020 | Inoue et al. | |
| 2008/0177189 A1 | 7/2008 | Kim et al. | |
| 2011/0299740 A1 | 12/2011 | Mori | |
| 2016/0324432 A1* | 11/2016 | Ahmed | A61B 5/0255 |
| 2017/0042433 A1* | 2/2017 | Noh | A61B 5/14542 |
| 2017/0112394 A1 | 4/2017 | Fujishiro | |
| 2017/0143265 A1* | 5/2017 | Hallberg | A61B 5/7221 |
| 2017/0347957 A1* | 12/2017 | van den Ende | H10N 30/20 |
| 2018/0035943 A1* | 2/2018 | Shemesh | A61B 5/7203 |
| 2019/0059752 A1* | 2/2019 | Botsva | A61B 5/332 |
| 2020/0138377 A1* | 5/2020 | Huijbregts | A61B 5/681 |

FOREIGN PATENT DOCUMENTS

| | | | |
|---|---|---|---|
| JP | 2016-026518 | 2/2016 | |
| JP | 6231216 | 11/2017 | |
| KR | 10-0859981 | 9/2008 | |
| KR | 10-0964559 | 6/2010 | |
| KR | 10-2016-0028093 | 3/2016 | |
| KR | 10-2017-0082255 | 7/2017 | |
| KR | 10-1756344 | 7/2017 | |
| KR | 10-2018-0016866 | 2/2018 | |
| WO | WO-2015184352 A1 * | 12/2015 | A61B 5/04 |

OTHER PUBLICATIONS

Taji et al., "Effect of Pressure on Skin-Electrode Impedance in Wearable Biomedical Measurement Devices", IEEE Transactions on Instrumentation and Measurement, vol. 67, No. 8, pp. 1900-1912, Aug. 2018. (Year: 2018).*

Office Action dated Aug. 8, 2023 in Korean Patent Application No. 10-2018-0163119 and English-language translation.

International Search Report for PCT/KR2019/013019, with English translation, mailed Jan. 14, 2020, 4 pages.

Written Opinion of the ISA for PCT/KR2019/013019 with English translation, mailed Jan. 14, 2020, 8 pages.

Office Action dated Feb. 20, 2024 in Korean Patent Application No. 10-2018-0163119 and English-language translation.

* cited by examiner

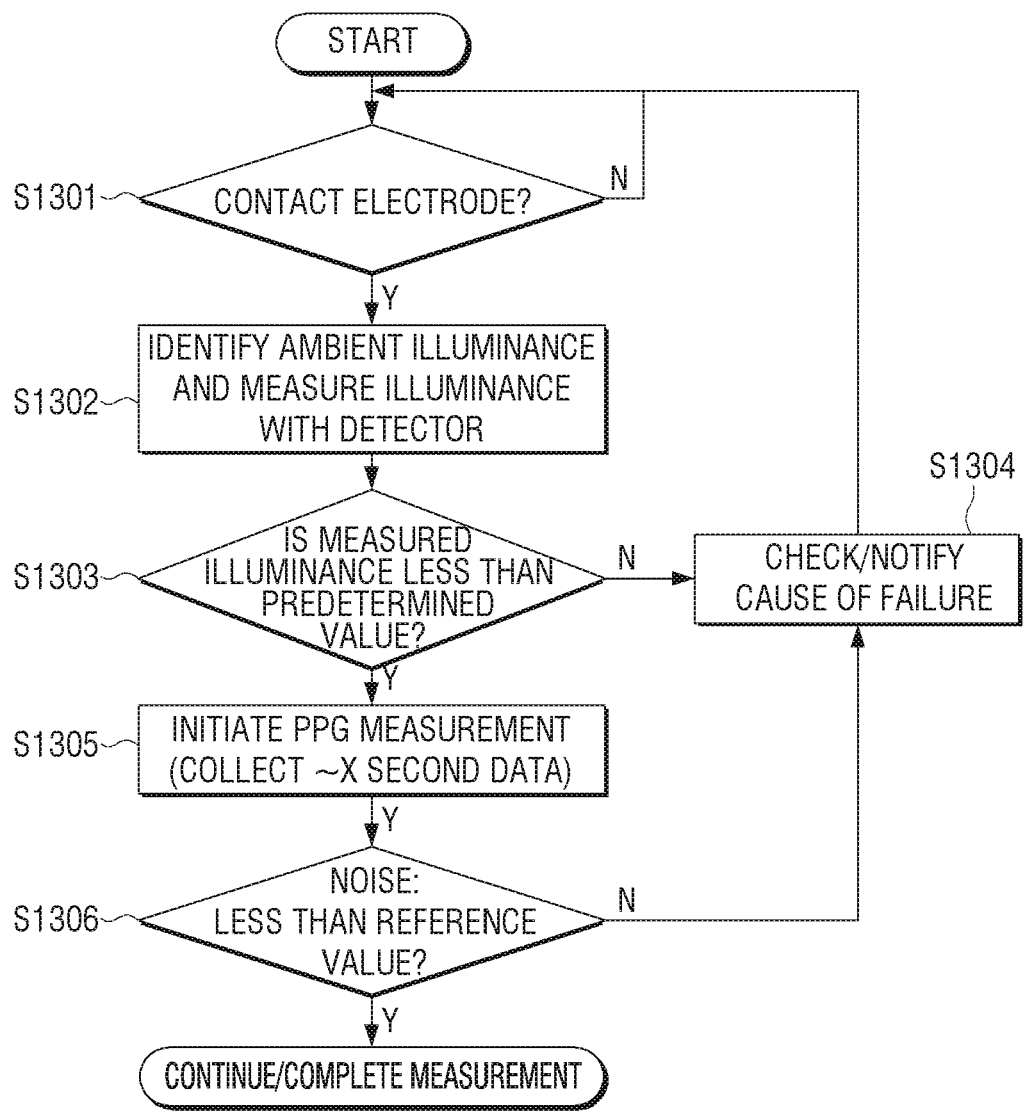

PPG SENSOR, ELECTRONIC DEVICE COMPRISING SAME, AND CONTROL METHOD THEREOF

BACKGROUND

Field

This disclosure relates to a Photoplethysmography (PPG) sensor, an electronic device including the same and a controlling method thereof and more particularly, to a PPG sensor including a transparent electrode window, an electronic device including the same and a controlling method thereof.

Description of Related Art

With the development of electronic technology, various types of electronic products have been developed and distributed. In particular, electronic products having a PPG sensor capable of measuring a user's physical condition have been commonly used.

The PPG sensor may acquire bio-signal information related to heart rate, blood vessels, etc. such as heart rate and stress index measurement using a predetermined number of light sources and detectors.

However, when the PPG sensor is not in complete contact with the body, it is impossible to measure a bio-signal. In addition, when the measurement is performed, a movement or a foreign substance causes a large amplitude noise and thus, a meaningless signal that cannot confirm the user's body condition is acquired.

Conventionally, when such a meaningless signal was acquired, the cause of the measurement failure could not be identified so that no result was acquired even after the user had waited for a long time unnecessarily, or the power was consumed quickly due to continuous measurement attempts, creating a problem that LED light is leaked to the outside.

SUMMARY

The disclosure has been made to solve the above-described problems, and an object of the disclosure is to provide a PPG sensor for quickly identifying a cause of an error in measurement of a bio-signal and providing feedback to a user, an electronic device including the same and a controlling method thereof.

According to an embodiment, an electronic device includes a Photoplethysmography (PPG) sensor including a light source, a detector and a transparent electrode window and a processor configured to, based on determining that a user is in contact with the PPG sensor based on a value sensed by the transparent electrode window, activate the detector, determine whether a contact between the PPG sensor and the user is poor based on an illuminance value sensed by the detector.

The electronic device may further include a display, and the processor may be configured to, based on an illuminance value sensed by the detector being less than a predetermined value, obtain biometric information of a user by activating the light source, and based on an illuminance value sensed by the detector being equal to or greater than a predetermined value, control the display to display a user interface screen for providing the user with information regarding a poor contact between the PPG sensor and the user.

The processor may be configured to, based on an illuminance value sensed by the detector being equal to or greater than a predetermined value, control the display to display a message intended to touch an entire area of the PPG sensor.

The electronic device may further include a memory and the processor may be configured to obtain a similarity between a first signal obtained by detector and a second signal of a normal range stored in the memory by comparing characteristics of the first signal obtained by the detector while the light source is activated and characteristics of the second signal, and based on the obtained similarity being less than a predetermined value, determine that there is an element interfering with sensing of the PPG sensor.

The processor may be configured to obtain the similarity by comparing at least one of a frequency, a first differential value or a second differential value of each of the first signal and the second signal.

The electronic device may further include a display and the processor may be configured to, based on a value sensed by the transparent electrode window being out of a predetermined range, control the display to display a message intended to touch the PPG sensor.

The electronic device may further include an illuminance sensor distinguished from the detector, and the processor may be configured to a reference value of an illuminance value sensed by the detector based on an ambient illuminance value sensed by the illuminance sensor.

The transparent electrode window may be configured to cover an upper part of the light source and the detector.

A Photoplethysmography (PPG) sensor according to an embodiment includes a light source, a detector configured to receive light and a transparent electrode window configured to cover an upper part of the light source and the detector.

The transparent electrode window may be configured to cover each of the upper part of the light source and the detector.

The PPG sensor may further include a plurality of metal electrodes, and the plurality of metal electrodes may be disposed one by one at both sides of the light source and the detector that are disposed side by side.

A controlling method of an electronic device comprising a Photoplethysmography (PPG) sensor including a light source, a detector and a transparent electrode window according to an embodiment includes, based on determining that a user is in contact with the PPG sensor based on a value sensed by the transparent electrode window, activating the detector and determining whether a contact between the PPG sensor and the user is poor based on an illuminance value sensed by the detector.

The method may further include, based on an illuminance value sensed by the detector being less than a predetermined value, obtaining biometric information of a user by activating the light source, and based on an illuminance value sensed by the detector being equal to or greater than a predetermined value, displaying a user interface screen for providing the user with information regarding a poor contact between the PPG sensor and the user.

The displaying may include, based on an illuminance value sensed by the detector being equal to or greater than a predetermined value, displaying a message intended to touch an entire area of the PPG sensor.

The method may further include obtaining a similarity between a first signal obtained by detector and a second signal of a normal range stored in the memory by comparing characteristics of the first signal obtained by the detector while the light source is activated and characteristics of the second signal, and based on the similarity being less than a predetermined value, determining that there is an element interfering with sensing of the PPG sensor.

The obtaining the similarity may include obtaining the similarity by comparing at least one of a frequency, a first differential value or a second differential value of each of the first signal and the second signal.

The method may further include, based on a value sensed by the transparent electrode window being out of a predetermined range, displaying a message intended to touch the PPG sensor.

The method may further include setting a reference value of an illuminance value sensed by the detector based on an ambient illuminance value sensed by the illuminance sensor.

The transparent electrode window may be configured to cover an upper part of the light source and the detector.

According to the above-described various embodiments, a PPG sensor for quickly identifying a cause of an error in measurement of a bio-signal and providing feedback to a user, an electronic device including the same and a controlling method thereof may be provided.

BRIEF DESCRIPTION OF THE DRAWINGS

FIG. 13 is a flowchart provided to explain a controlling method of an electronic device according to an embodiment in greater detail.

DETAILED DESCRIPTION

Figures 1A, 1B:
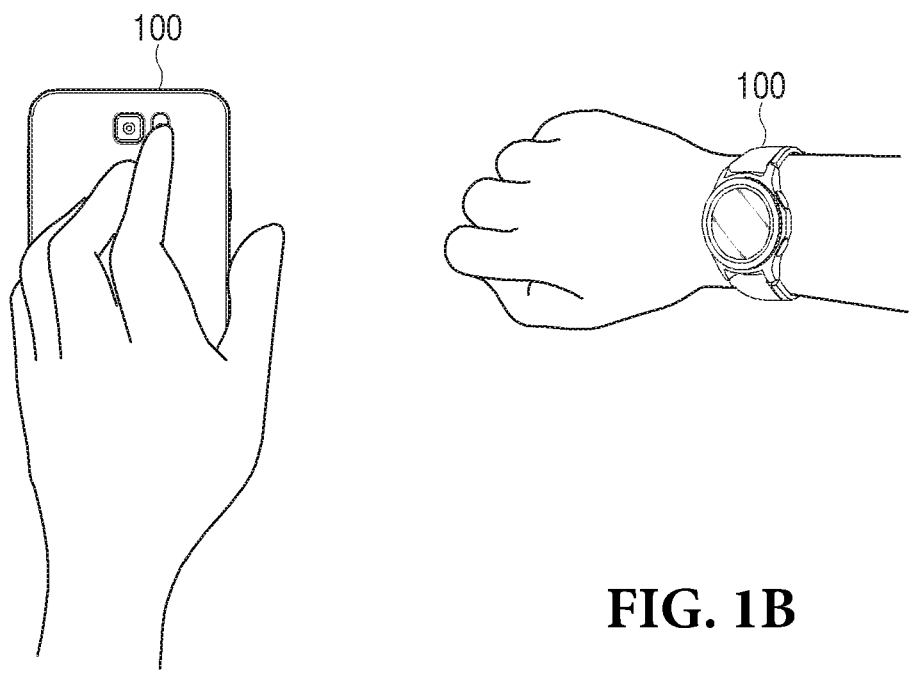
FIG. 1 is a view illustrating an example of use of an electronic device according to an embodiment.

After terms used in the specification are briefly described, the disclosure will be described in detail.

General terms that are currently widely used were selected as terms used in embodiments of the disclosure in consideration of functions in the disclosure, but may be changed depending on the intention of those skilled in the art or a judicial precedent, an emergence of a new technique, and the like. In addition, in a specific case, terms arbitrarily chosen by an applicant may exist. In this case, the meaning of such terms will be mentioned in detail in a corresponding description portion of the disclosure. Therefore, the terms used in the disclosure should be defined on the basis of the meaning of the terms and the contents throughout the disclosure rather than simple names of the terms.

Embodiments of the disclosure may apply various modifications and have various embodiments, and specific embodiments will be illustrated in the drawings and described in detail in the detail description. However, this is not intended to limit the scope to the specific embodiment, and it should be understood to include all modifications, equivalents, and substitutes included in the scope of the disclosed spirit and technology. In describing the embodiments, when it is determined that the detailed description of the related known technology may obscure the gist, the detailed description thereof will be omitted.

Terms 'first', 'second', and the like, may be used to describe various components, but the components are not to be construed as being limited by the terms. The terms are used only to distinguish one component from other components.

Singular expressions include plural expressions unless the context clearly indicates otherwise. It should be further understood that terms "include" or "constitute" used in the application specify the presence of features, numerals, steps, operations, components, parts, or combinations thereof mentioned in the specification, but do not preclude the presence or addition of one or more other features, numerals, steps, operations, components, parts, or combinations thereof.

In the present disclosure, 'module' or 'part' performs at least one function or operation, and may be implemented as hardware or software, or a combination of hardware and software. Further, except for when each of a plurality of 'modules' and 'parts' needs to be realized in a specific hardware, 'modules' or 'parts' may be integrated in at least one module and may be realized in at least one processor.

Hereinafter, embodiments of the disclosure will be described in detail with reference to the accompanying drawings so that those skilled in the art to which the disclosure pertains may easily practice the disclosure. However, the disclosure may be implemented in various different forms and is not limited to embodiments described herein. In addition, in the drawings, portions unrelated to the description will be omitted, and similar portions will be denoted by similar reference numerals throughout the specification and drawings.

Hereinafter, embodiments will be described in detail with reference to the accompanying drawings.

FIG. 1 is a view illustrating an example of use of an electronic device according to an embodiment. Specifically, FIG. 1(A) illustrates a case in which an electronic device 100 is a smartphone, and FIG. 1(B) illustrates a case in which the electronic device 100 is a smart watch.

Referring to FIG. 1(A), when a user needs to measure a bio-signal, the user may measure the bio-signal by placing a finger which is a part of the body on a PPG sensor. In this case, the measurement of the biometric sensor may not be performed smoothly due to various causes such as when the user does not cover the entire area of the PPG sensor, when the user's finger is not in complete contact with the PPG sensor, when foreign substances are attached to the surface of the PPG sensor, when the user's body moves during measurement, etc.

Meanwhile, referring to FIG. 1(B), the PPG sensor may be disposed at a portion where the electronic device 100 is in contact with the wrist, and the electronic device 100 may measure the user's bio-signal at predetermined intervals. In this case, the measurement of the biometric sensor may not be performed smoothly due to various causes such as when the user's body does not cover the entire area of the PPG sensor, when the user's finger is not in complete contact with the PPG sensor, when foreign substances are attached to the surface of the PPG sensor, when the user's body moves during measurement, etc.

In the present disclosure, one of various causes of failure in measuring the bio-signal may be identified through a series of operations as described above and provided to the user. The specific operations of the electronic device 100 will be described in detail with reference to FIGS. 2 to 13.

Meanwhile, although FIG. 1 illustrates that the electronic device 100 is a smartphone or a smart watch, but the electronic device 100 is not limited thereto. The electronic device 100 may be any wearable device capable of contacting a part of the user's body such as a smart band, a smart glasses, etc.

Figure 2:
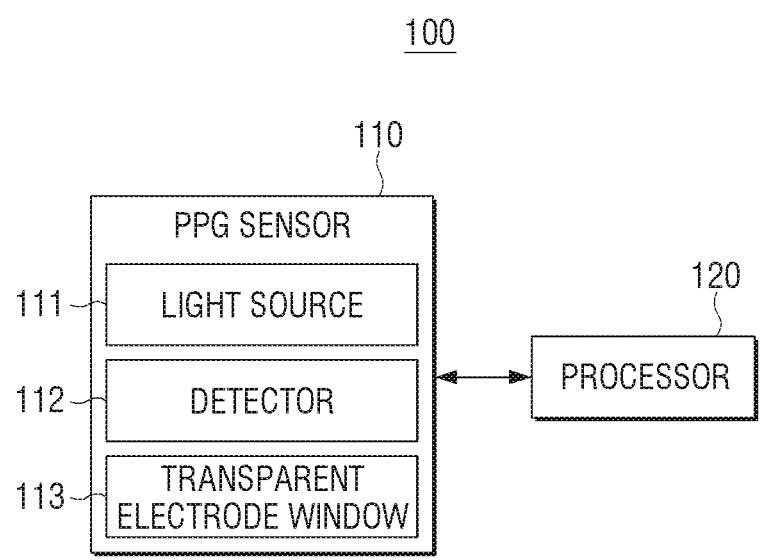
FIG. 2 is a block diagram provided to explain configuration of an electronic device briefly according to an embodiment.

FIG. 2 is a block diagram provided to explain configuration of an electronic device briefly according to an embodiment.

Referring to FIG. 2, the electronic device 100 includes a PPG sensor 110 and a processor 120.

The PPG sensor 110 is a sensor for measuring a bio-signal through an optical method using a light source 111 and a detector 112, and may measure heart rate, oxygen saturation, blood pressure, Heart Rate Variability (HRV), vascular disease, etc.

Specifically, the light source is configured to emit light. For example, the light source 111 may be at least one of an LED or a laser diode. Hereinafter, there is a portion in which the light source 111 will be described as an LED for convenience of explanation, but the light source 111 is not limited thereto.

In this case, the light emitted from the light source 111 may be green light. The light emitted from the light source 111 may be partially absorbed, scattered and reflected by the user's skin and blood vessels, and may be sensed by the detector 112.

Here, the detector 112 is configured to sense ambient light, and may be at least one of a Photo Diode (PD) or a Charge Coupled Device (CCD). The signal sensed by the detector 112 is proportional to the amount of blood and thus, it is possible to detect a change in the amount of blood based on a change in the signal. Hereinafter, there is a portion in which the detector 112 is described as a PD for convenience of explanation, but the detector 112 is not limited thereto.

Meanwhile, the signal sensed by the detector 112 may be a signal in which an AC component and a DC component are mixed and in this case, the AC component may be obtained by a change in the amount of blood at the measured site.

Figure 4:
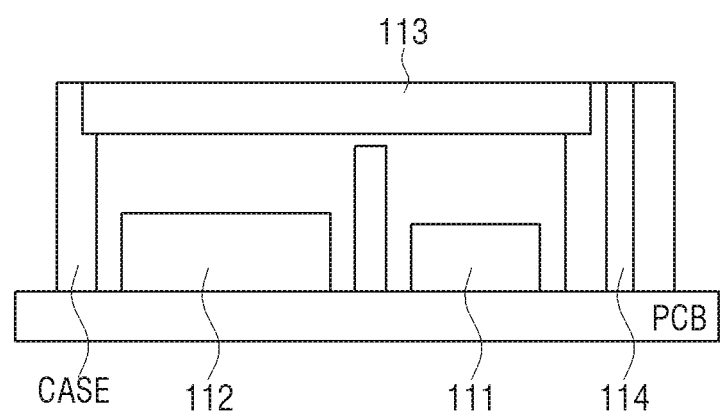
FIG. 4 is a view provided to explain a structure of a PPG sensor according to an embodiment.
Figure 8:
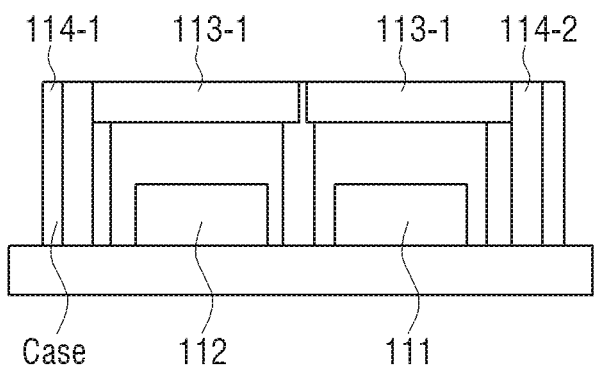
FIGS. 8 and 9 are views provided to explain a structure of a PPG sensor according to another embodiment.
Figure 9:
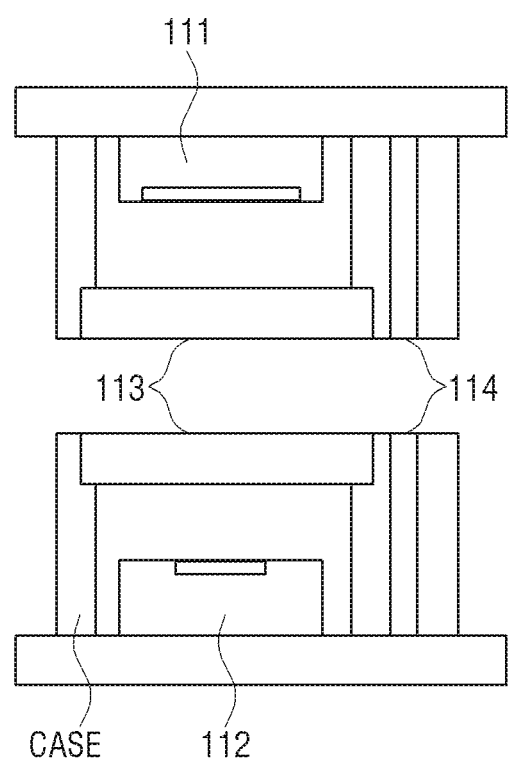

Meanwhile, a transparent electrode window 113 may be disposed to cover upper portions of the light source 111 and the detector 112. Specifically, the transparent electrode window 113 may be in an integrated form covering both of the upper portions of the light source 111 and the detector 112 as illustrated in FIG. 4, or may be in a separate form covering each of the upper portions of the light source 111 and the detector 112 separately as illustrated in FIGS. 8 and 9.

When the transparent electrode window 113 is in contact with the user's body part, current flows or a voltage is applied. In this case, whether the user's body part is in contact may be identified based on at least one of the measured current, voltage, impedance value, or conductivity. Specifically, the transparent electrode window 113 may be any material used as a transparent electrode such as Indium Tin Oxide (ITO), metal mesh, metal nanowire, carbon nanotube (CNT), fluorine doped tin oxide (FTO), etc. Here, the conditions of the transparent electrode may be a transmittance of visible light of 80% or more, a sheet resistance of 1000 $\Omega$/sq or less, or a conductivity of 1000 S/m or more.

In this case, the transparent electrode window 113 may be composed of only a transparent electrode material itself, but may be configured in a form in which a transparent electrode material is disposed on the surface of an existing glass or plastic window.

The processor 120 controls the overall operations of the electronic device 100.

According to an embodiment, the processor 120 may be implemented as a digital signal processor (DSP) processing a digital signal, a microprocessor, or a time controller (TCON). However, the processor 120 is not limited thereto, but may include one or more of a central processing unit (CPU), a micro controller unit (MCU), a micro processing unit (MPU), a controller, an application processor (AP), a communication processor (CP), or an ARM processor, or may be defined by these terms. In addition, the processor 120 may be implemented as a system-on-chip (SoC) or a large scale integration (LSI) in which a processing algorithm is embedded or may be implemented in a field programmable gate array (FPGA) form.

Specifically, the processor 120 may determine whether the PPG sensor 110 is in contact with a user based on a value sensed by the transparent electrode window 113. Specifically, if the value sensed by the transparent electrode window 113 is out of a predetermined range, the processor 120 may determine that the PPG sensor 110 is not in contact with the user's body part. In this case, the processor 120 may determine whether the user is in contact using at least one of the current value, voltage value, impedance and conductivity sensed by the transparent electrode window 113.

For example, if the current value sensed by the transparent electrode window 113 is less than a predetermined value, the processor 120 may determine that the PPG sensor 110 is not in contact with the user's body part. In this case, the processor 120 may not perform any separate operation until the user's body part is in contact with the transparent electrode window 113, or may provide a message requesting the user to contact the PPG sensor 110.

Meanwhile, if the value sensed by the transparent electrode window 113 is within the predetermined range, the processor 120 may determine that the user's body part is in contact. For example, if the current value sensed by the transparent electrode window 113 is equal to or greater than the predetermined value, the processor 120 may determine that the user's body part is in contact. In this case, the processor 120 may measure the illuminance of the surrounding environment by activating the detector 112.

Here, activating the detector 112 may be controlling the detector 112 which has not received light, to receive light. Alternatively, activating the detector 112 may mean that before the activation, even if light is received, the received light is not processed, whereas after the activation, an illuminance value is acquired by processing the received light. In addition, the illuminance measurement through activation of the detector 112 is characterized in that the measurement is performed in a state where the light source 111 for PPG such as an LED is not turned on.

The processor 120 may determine whether there is a poor contact between the PPG sensor 110 and the user based on the illuminance value sensed by the detector 112.

Specifically, if the illuminance value sensed by the detector 112 is equal to or greater than a predetermined value, the processor 120 may determine that the contact is defective, such as when only a part of the PPG sensor 110 is in close contact with the user's body part, and provide a message requesting the user to contact the PPG sensor 110 again.

Meanwhile, if the illuminance value sensed by the detector 112 is less than the predetermined value, the user's bio-signal can be obtained by activating the light source 111.

As described above, by activating the configuration of the PPG sensor 110 step by step to identify the cause of the measurement failure, it is possible to identify and correct the cause more quickly and accurately, thereby minimizing power consumption.

Figure 3:
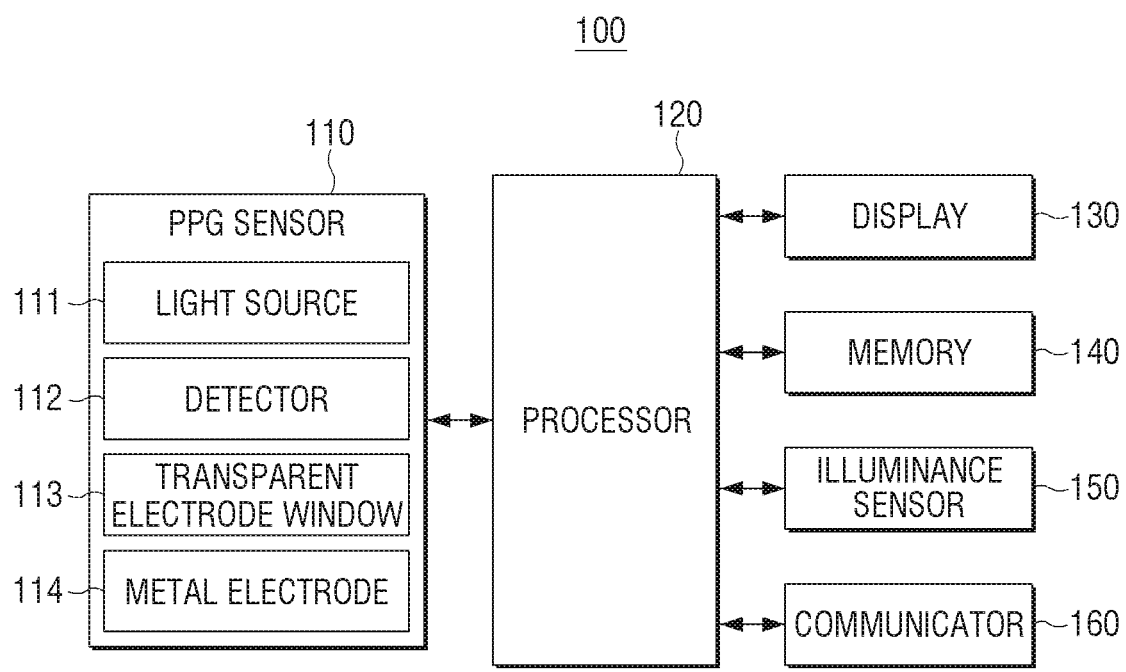
FIG. 3 is a block diagram provided to explain specific configuration of the electronic device illustrated in FIG. 2.

FIG. 3 is a block diagram provided to explain specific configuration of the electronic device illustrated in FIG. 2.

Referring to FIG. 3, the electronic device 100 may include the PPG sensor 110, the processor 120, a display 130, a memory 140, an illuminance sensor 150, and a communicator 160.

Here, some configurations and operations of the PPG sensor 110 and the processor 120 are the same as those illustrated in FIG. 2 and thus, overlapping descriptions will be omitted.

The PPG sensor 110 may further include a metal electrode 114 in addition to the light source 111, the detector 112 and the transparent electrode window 113. When the user's body part is in contact with both the transparent electrode window 113 and the metal electrode 114, current is generated, and the processor 120 may determine whether the user is in contact based on the measured current value. In this case, elements that can be used as the metal electrode 114 include Group I elements such as aluminum (Al), copper (Cu), lithium (Li), sodium (Na), potassium (K), Rubidium (Ru), cesium (Cs), francium (Fr), etc. Group II elements such as beryllium (Be), magnesium (Mg), calcium (Ca), strontium (Sr), barium (Ba), radium (Ra), etc., lead (Pb), nickel (Ni), copper (Cu), aluminum (Al), titanium (Ti), Steel Use Stainless (SUS), iron-based alloys, etc.

In addition, additional biometric information measurement can be performed by the transparent electrode window 113 and the metal electrode 114. Specifically, the processor 120 may further perform GSR, BIA, capacitive fingerprint recognition, pressure sensing, and temperature sensing based on the impedance and capacitance value obtained by the transparent electrode window 113 and the metal electrode 114. For example, when both PPG and pressure are measured at the same time, it is possible to check whether excessive contact pressure interferes with sensing.

The display 130 may display contents. Specifically, the display 130 may display contents under the control of the processor 120.

The display 130 may be implemented as various types of displays such as Liquid Crystal Display (LCD), Organic Light Emitting Diodes (OLED) display, Plasma Display Panel (PDP), etc. The display 130 may further include a driving circuit, a backlight unit and the like, that may be implemented in a form such as a-si TFT, low temperature poly silicon (LTPS) TFT, an organic TFT (OTFT), and the like. In addition, the display 130 may be implemented as a touch screen, a flexible display or a transparent display.

The display 130 may display a message to be provided to a user under the control of the processor 120. Specifically, if it is determined that a contact between the PPG sensor 110 and the user's body part is poor, the processor 120 may control the display 130 to display a user interface (UI) screen for providing the user with information regarding the poor contact.

For example, if the user's contact on the transparent electrode window 113 is not sensed, the processor 120 may control the display 130 to display a message requesting a contact with the PPG sensor 110.

In another embodiment, if the illuminance value sensed by the detector 112 is equal to or greater than a predetermined value, the processor 120 may control the display 130 to display a message requesting that the user's body part covers the entire PPG sensor 110.

In another embodiment, if the similarity between the bio-signal obtained through the PPG sensor 110 and the bio-signal of the normal range stored in the memory 130 is less than a predetermined value, the processor 120 may control the display 130 to display a message requesting the user not to move during measurement, to remove foreign substances on the surface of the PPG sensor 110, not to strongly press the surface of the PPG sensor 110, etc. In this case, if an acceleration sensor or a pressure sensor is included in the electronic device, the processor 120 may provide the cause of the PPG measurement failure in greater detail by further considering the measured value of the acceleration sensor. For example, if the value sensed by the acceleration sensor is equal to or greater than a predetermined value, the electronic device may determine that the cause of the signal failure of the PPG sensor 110 is due to movement during measurement by further considering the sensed value. Alternatively, if the value sensed by the pressure sensor is equal to or greater than a predetermined value, the electronic device may determine that the cause of the signal failure of the PPG sensor 110 is due to excessive pressure on the surface of the PPG sensor 110 by further considering the sensed value.

Meanwhile, although not illustrated in FIG. 3, the electronic device 100 may further include a speaker (not shown), and the processor 120 may provide a message to the user through the speaker.

The memory 140 may store various programs and data necessary for the operation of the electronic device 100. Specifically, at least one command may be stored in the memory 140. The processor 120 may perform the above-described operation by executing a command stored in the memory 140. The memory 140 may be implemented as a non-volatile memory, a volatile memory, a flash memory, a hard disk drive (HDD), a solid state drive (SSD), or the like.

Specifically, the memory 140 may store a bio-signal of a normal range. Specifically, the memory 140 may store an original signal, a first differential signal and a second differential signal of the bio-signal of the normal range. Here, information on the bio-signal stored in the memory 140 may be a waveform itself or information on the characteristics of each signal.

In this case, the memory 140 may store a bio-signal of a normal range for each user.

The processor 120 may obtain a similarity by comparing the characteristics of a signal obtained by the detector 112 while the light source 111 is activated and a signal of a normal range stored in the memory 140. If the obtained similarity is less than a predetermined value, the processor 120 may determine that there is an element that interferes with the sensing of the PPG sensor 110. Specifically, the processor 120 may obtain a similarity by comparing the obtained signal with at least one of the frequency of a signal of a normal range stored in the memory 140, a first differential value or a second differential value. Here, the processor 120 may obtain the similarity by comparing at least one of the frequency, period, waveform, rate of change, Zero-Crossing Rate (ZCR), maximum value, or minimum value of the signal.

If the obtained similarity is less than a predetermined value, the processor 120 may determine that there is an element that interferes with the sensing of the PPG sensor 110 and provide information on this to a user so as to request the user to change the measurement state. Specifically, the processor 120 may provide the user with a message requesting not to move during measurement, to remove foreign substances from the surface of the PPG sensor 110, not to strongly press the surface of the PPG sensor, etc. through the display 130 or a speaker (not shown).

The illuminance sensor 150 is designed to sense illuminance of the surrounding environment, and may be a component separate from the detector 112. Specifically, the illuminance sensor 150 may be disposed on the outer surface of the electronic device 100 and sense illuminance of the surrounding environment of the electronic device 100.

The processor 120 may set a reference of the illuminance value of the detector 112 to determine a poor contact based on the value sensed by the illuminance sensor 150. In this case, sensing by the detector 112 may be performed while the light source 111 is inactivated.

Specifically, based on the value sensed by the illuminance sensor 150, when the surrounding environment is dark, the processor 120 may set the reference of the illuminance value of the detector 112 lower than when it is bright.

Meanwhile, in the present disclosure, the illuminance sensor 150 may be omitted, and if the illuminance sensor 150 is not provided, the illuminance of the surrounding environment may be sensed by the detector 112.

The communicator 160 is configured to perform communication with various types of external devices according to various types of communication methods. The electronic device 100 may communicate with a server which is an external device, through the communicator 160. According to an embodiment, some of the operations of the electronic device 100 may be performed by the server.

For example, the processor 120 may transmit the value sensed by the transparent electrode window 113, the detector 112, etc. to the server through the communicator 160, receive a message regarding a measurement failure from the server and provide the message to a user through the display 130 or a speaker (not shown). Alternatively, the processor 120 may receive an operation command from the server through the communicator 160, and perform an operation corresponding to the operation command.

FIG. 4 is a view provided to explain a structure of a PPG sensor according to an embodiment. Specifically, FIG. 4 is a side view of the PPG sensor according to an embodiment.

Referring to FIG. 4, in the PPG sensor 110, the light source 111 that emits light and the detector 112 that receives light may be arranged side by side on a PCB substrate. Here, a case may be formed to surround side surfaces of the light source 111 and the detector 112 disposed on the PCB substrate. In addition, the light source 111 and the detector 112 may be spatially separated through a partition.

The transparent electrode window 113 may be disposed to cover the light source 111 and the detector 112. Specifically, the transparent electrode window 113 may be disposed on a side opposite to one side of the case on which the PCB substrate is disposed. For example, if the PCB substrate is disposed on the lower side of the case, the transparent electrode window 113 may be disposed on the upper side of the case.

In this case, the transparent electrode window 113 may be disposed to cover the upper sides of both the light source 111 and the detector 112. Here, the transparent electrode window 113 may be configured in an integrated form covering the upper sides of both the light source 111 and the detector 112 with one transparent electrode window as illustrated in FIG. 4. In another embodiment, the transparent electrode window 113 may be provided in a separate form covering the upper side of the light source 111 and the detector 112 separately with a plurality of transparent electrode windows, as shown in FIGS. 8 and 9.

In addition, a metal electrode 114 may be included on one side of the case. In this case, the metal electrode 114 may be exposed on the upper surface, and may be in direct contact with a user. If the user touches the transparent electrode window 113 and the metal electrode 114 simultaneously, the electronic device may determine whether the user is in contact through the current, voltage, impedance, and conductivity measured by the touch.

In FIG. 4, only one metal electrode 114 is illustrated, but a plurality of metal electrodes may be included as illustrated in FIG. 8.

Figure 5:
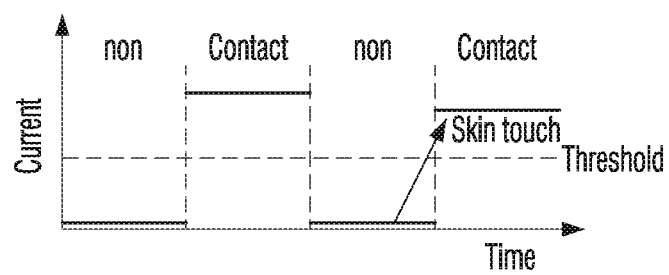
FIG. 5 is a view provided to explain a current sensed according to a contact between a user and a PPG sensor according to an embodiment.

FIG. 5 is a view provided to explain a current sensed according to a contact between a user and a PPG sensor according to an embodiment. Specifically, the electronic device may determine whether the user is in contact based on the current value sensed according to a contact between the user and the PPG sensor.

Referring to FIG. 5, if there is no user contact on the PPG sensor, the sensed current value is less than a predetermined threshold value, and if there is a user contact on the PPG sensor, a current value greater than the predetermined threshold value is identified. In this case, the sensed current value may vary depending on the size where the PPG sensor and the user come into contact. Accordingly, the electronic device may determine there is a meaningful contact only when the sensed current value is equal to or greater than the predetermined value.

Figure 6:
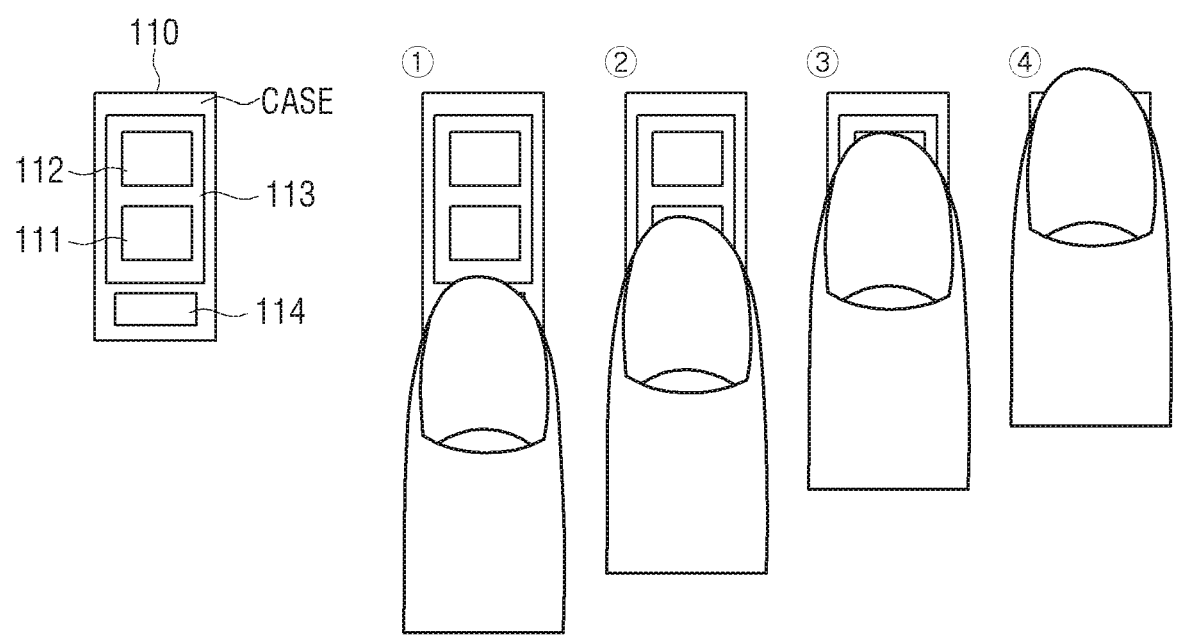
FIG. 6 is a view provided to explain various embodiments of a poor contact between the PPG sensor of FIG. 5 and the user.

FIG. 6 is a view provided to explain various embodiments of a poor contact between the PPG sensor and the user. Firstly, the PPG sensor illustrated in FIG. 6 is a top view of the PPG sensor according to an embodiment.

Referring to FIG. 6, the PPG sensor 110 includes the light source 111, the detector 112 that is arranged alongside the light source 111, the transparent electrode window 113 covering the upper sides of the light source 111 and the detector 112, and the metal electrode 114. In this case, the light source 111, the detector 112 and the metal electrode 114 may be arranged in a row in a longitudinal direction. This arrangement is based on a user's gripping type when the electronic device is a smartphone, and is not limited thereto. In case that the electronic device is a wearable device such as a smart watch, the arrangement order or direction may be changed. In addition, the shape of the configuration is not limited to a square. If an LED is circular, the detector may be provided in a ring shape centered on the circular LED.

Meanwhile, as it goes from ① to ④, the contact area between the user and the PPG sensor 110 may increase. Specifically, ① is when the user touches only the metal electrode 114, ② is when the user touches an area corresponding to a part of the light source 111 out of the metal electrode 114 and the transparent electrode window 113, ③ is when the user touches an area corresponding to a part of the light source 111 and the detector 112 out of the metal electrode 114 and the transparent electrode window 113, and ④ is when the user touches the entire area of the metal electrode 114, the light source 111 and the detector 112 out of the transparent electrode window 113.

Figures 7A, 7B:
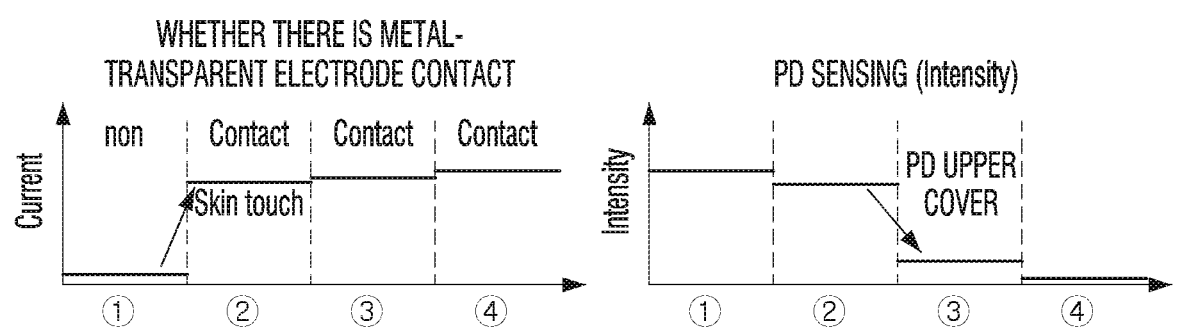
FIG. 7 is a view provided to explain a current and an intensity of light measured in the various embodiments of poor contact illustrated in FIG. 6.

In this case, as illustrated in FIG. 7(A), different current values may be sensed according to the contact area. Specifically, in the case of ① where the user touches only the metal electrode 114 and does not touch the transparent electrode window 113, the sensed current may be very low.

From ② where both the metal electrode 114 and the transparent electrode window 113 are touched, a meaningful current value which is equal to or greater than a predetermined threshold value is sensed, and the electronic device may determine that the user is in contact with the PPG sensor 110. In this case, if the detector 112 is in an inactivated state, when determining that the user is in contact, the electronic device may activate the detector 112.

In the case of ③ and ④ where the contact area between the user and the PPG sensor 110 gradually increases, the sensed current value increases in comparison with ②, and the electronic device may determine whether the contact is poor based on the sensed current value. Meanwhile, the electronic device may determine whether the contact between the user and the PPG sensor 110 is poor by further using the illuminance value sensed by the detector 112.

Specifically, as illustrated in FIG. 7(B), based on the intensity value of illuminance sensed by the detector 112 (e.g., photodiode (PD)) according to the contact area between the user and the PPG sensor 110, it may be determined whether the contact between the user and the PPG sensor 110 is poor or not. Specifically, in the case of ① and ②, the user does not block the detector 112 and thus, a high illuminance value may be sensed. In this case, the detector 112 may be already activated and here, the sensed illuminance value may be similar to the illuminance value of the surrounding environment.

Meanwhile, in an embodiment where the user comes in contact with the PPG sensor 110 while the detector 112 is inactivated, in the case of ①, an illuminance value may not be sensed as the detector is in the inactivated state. Here, in the case of ② to ④, as the transparent electrode window 113 is touched while the detector 112 is in an inactivated state, the detector 112 may be in an activated state.

In the case of ③ and ④ where at least part of the detector 113 is covered by the user, the sensed illuminance value may be very low. In this case, if the sensed illuminance value is less than a predetermined value, the electronic device may obtain biometric information by activating the light source 111. Here, the predetermined value means an illuminance value that is sensed when the user contacts the PPG sensor 110 so as to obtain the biometric information of the user, and may vary depending on the illuminance value of the surrounding environment. For example, when the surrounding environment is dark, the predetermined value may be lower than when it is bright.

FIG. 8 is a view provided to explain a structure of a PPG sensor according to another embodiment. Specifically, the PPG sensor 110 illustrated in FIG. 8 includes a plurality of metal electrodes 114-1, 114-2 and a plurality of transparent electrode windows 113-1, 113-2 covering the light source 111 and the detector 112, respectively.

Here, the plurality of metal electrodes 114-1, 114-2 may be disposed at each side of the light source 111 and the detector 112 which are arranged side by side.

As illustrated in FIG. 8, with the plurality of transparent electrode windows 113-1, 113-2 that are separated by area, the area in contact with the user may be identified more specifically.

In addition, as illustrated in FIG. 8, with the plurality of metal electrodes 114-1, 114-2, it is possible to measure impedance of several electrode configurations according to a contact with the user, and it is possible to determine whether the contact between the PPG sensor 110 and the user is poor or not based on the impedance measurement value without using an illuminance value by the detector 112.

FIG. 9 is a view provided to explain a structure of a PPG sensor according to yet another embodiment. While FIGS. 4 and 8 illustrates a reflective structure in which the light emitted from the light source 111 is reflected on the user's skin, and the reflected light is sensed by the detector 112, FIG. 9 illustrates a transmissive structure in which the light emitted from the light source 111 passes through the user's skin and is sensed by the detector 112.

Referring to FIG. 9, the light source 111 and the detector 112 may be disposed on a separate PCB substrate, and a light emitting unit of the light source 111 and a light receiving unit of the detector 112 may face each other with a predetermined interval in-between. Here, the predetermined interval may mean a degree to which a user's body part can fit within the interval. FIG. 9 illustrates that the light source 111 is disposed at the upper part and the detector 112 is disposed at the lower part, but the light source 111 may be disposed at the lower part and the detector 112 may be disposed at the upper part.

The transparent electrode window 113 may be disposed on the upper part of at least one of the light source 111 and the detector 112, and when being disposed on only one side, the transparent electrode window 113 may be disposed at a lower part for an easy touch by a user. In FIG. 9, the detector 112 is disposed at a lower part and thus, when the transparent electrode window 113 is disposed on only one side, it may be disposed to cover the upper part of the detector 112.

Meanwhile, the arrangement of the metal electrode 114 may be changed according to the arrangement shape of the transparent electrode window 113. Specifically, the metal electrode 114 is disposed in the area where the transparent electrode window 113 is disposed, and when the transparent electrode window 113 is disposed at the upper part of the light source 111 and the detector 112, respectively, the metal electrode 114 may also be disposed at both sides. In this case, even if the transparent electrode window 113 is disposed at both sides, the metal electrode 114 may be disposed only at one side to sense a user's contact only at the side where the metal electrode 114 is disposed.

FIG. 10 is a view provided to explain an embodiment of determining whether there is an element interfering with sensing of a PPG sensor according to signal quality.

Figure 10A:
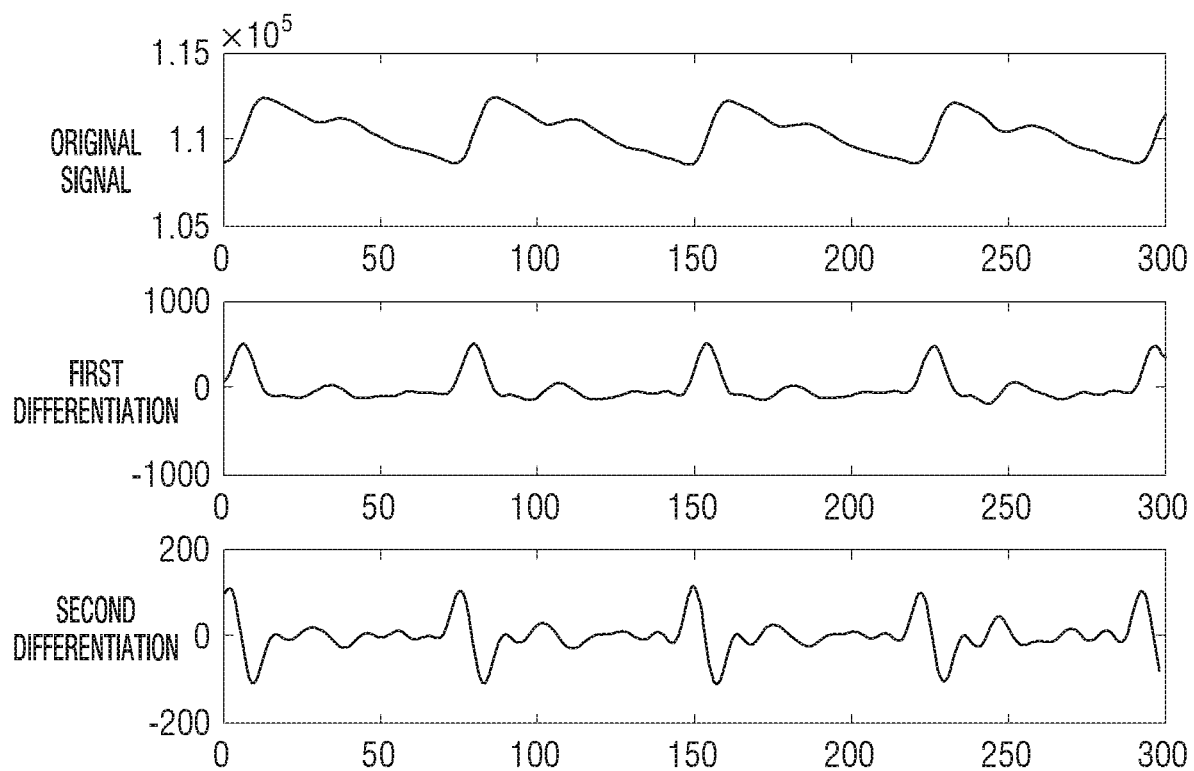
FIG. 10 is a view provided to explain an embodiment of determining whether there is an element interfering with sensing of a PPG sensor according to signal quality.

FIG. 10(A) illustrates an original signal, a first differential signal and a second differential signal of a bio-signal of a normal range. Such a bio-signal of a normal range may be pre-stored in a memory of an electronic device. According to an embodiment, a bio-signal of a normal range may be stored for each user.

Figure 10B:
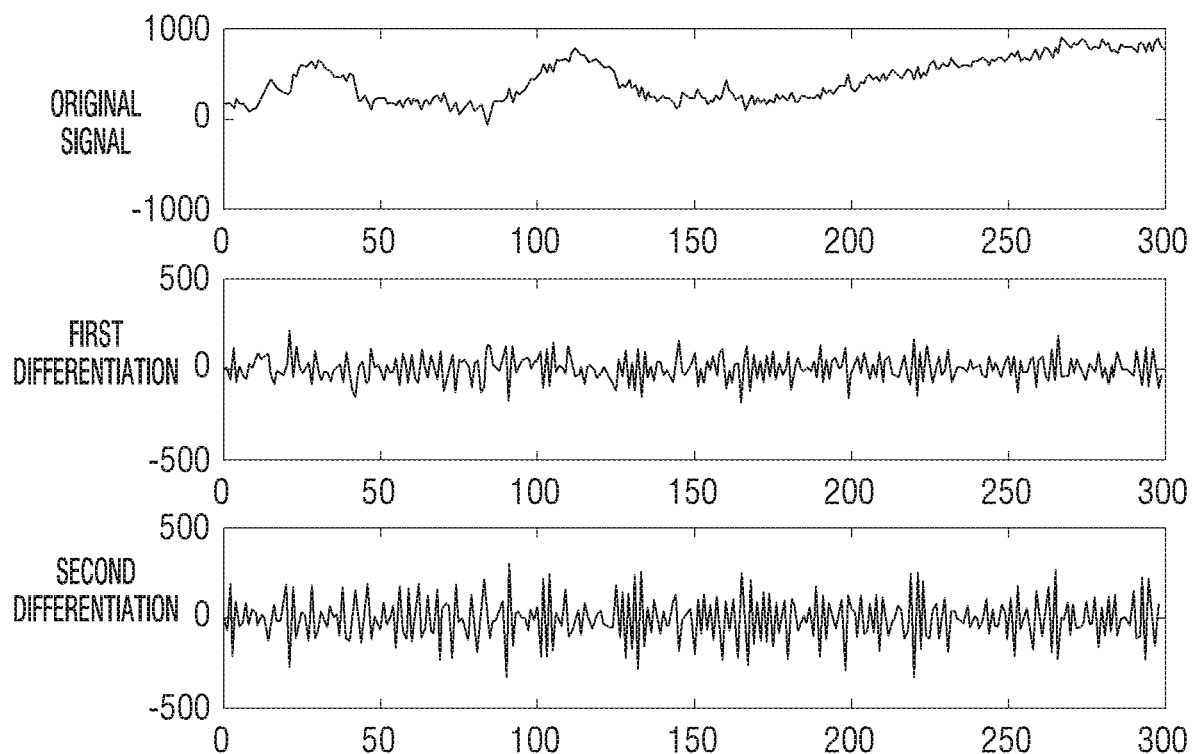

Meanwhile, even if it is determined that there is no problem in the contact between the PPG sensor and the user based on an illuminance value sensed by the transparent electrode window and the detector, a bio-signal may not be obtained normally as illustrated in FIG. 10(B). In this case, the electronic device may determine whether there is a noise in the bio-signal obtained by the PPG sensor.

Specifically, the electronic device may identify the quality of the obtained signal by analyzing signal characteristics of the bio-signal obtained by the PPG sensor and a pre-stored bio-signal. For example, the electronic device may obtain a similarity between the obtained signal and the bio-signal of the normal range through frequency component analysis, differential value analysis, analysis of Zero-Crossing Rate (ZCR) that distinguishes noise, etc.

In this case, if it is determined that the quality of the obtained bio-signal is low, the electronic device may determine that there is an element interfering with sensing of the PPG sensor. Specifically, if the obtained similarity is less than a predetermined value, the electronic device may quickly request re-measurement by providing a correction guide through the analyzed result. For example, based on the signal analysis result, the electronic device may provide a user with a guide that advises the user not to move during measurement, to remove foreign substances on the surface of the PPG sensor, to control contact pressure with the PPG sensor, not to press the surface of the PPG sensor strongly, etc. For example, if acceleration or contact pressure is measured at the same time as the PPG sensor, the electronic device may guide the user about the cause of the signal failure in greater detail.

Figure 11:
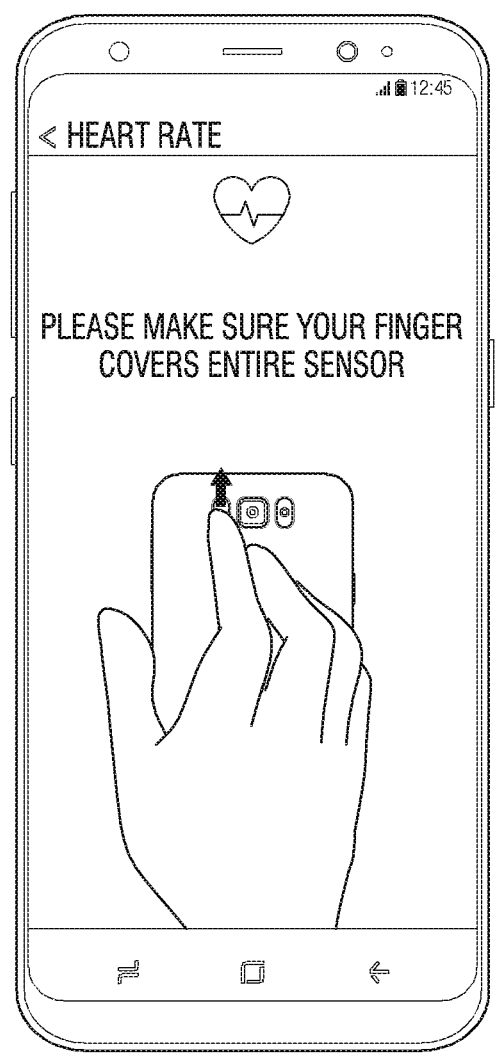
FIG. 11 is a view illustrating an embodiment of a User Interface (UI) screen provided to a user when it is determined that there is a poor contact between a PPG sensor and a user.

FIG. 11 is a view illustrating an embodiment of a User Interface (UI) screen provided to a user when it is determined that there is a poor contact between a PPG sensor and a user.

Referring to FIG. 11, the electronic device 100 may display a UI screen requesting the user to cover the entire surface of the PPG sensor with his or her finger. Specifically, while displaying a text message of "please make sure the finger covers the entire sensor", the electronic device may provide a method of correcting a touch position more intuitively by providing an image or an animation.

Meanwhile, the UI screen illustrated in FIG. 11 may be displayed in a case where although a user touches the PPG sensor, the touch does not cover the PPG sensor enough to measure a bio-signal. In this case, a UI including the area of the sensor that is actually covered by the finger based on the level of the illuminance value or the measured current value may be provided to the user (e.g., different images/animations may be provided depending on the degree of coverage such as half or ¼ of the sensor).

Therefore, in an actual embodiment, if a contact is not sensed at a time when a bio-signal should be measured using the PPG sensor, the electronic device 100 may display a message with the intention of "please touch the PPG sensor." Meanwhile, in a case where the user's contact is sensed but the PPG sensor is not entirely covered based on a result of illuminance sensing, the electronic device may request to cover the entire PPG sensor. In addition, in a case where a bio-signal of a normal range is not obtained in spite of a good contact between the PPG sensor and the user, the electronic device 100 may display a message such as "please do not move during measurement", "please remove foreign substances on the PPG sensor", "please do not press the PPG sensor strongly", etc.

Figure 12:
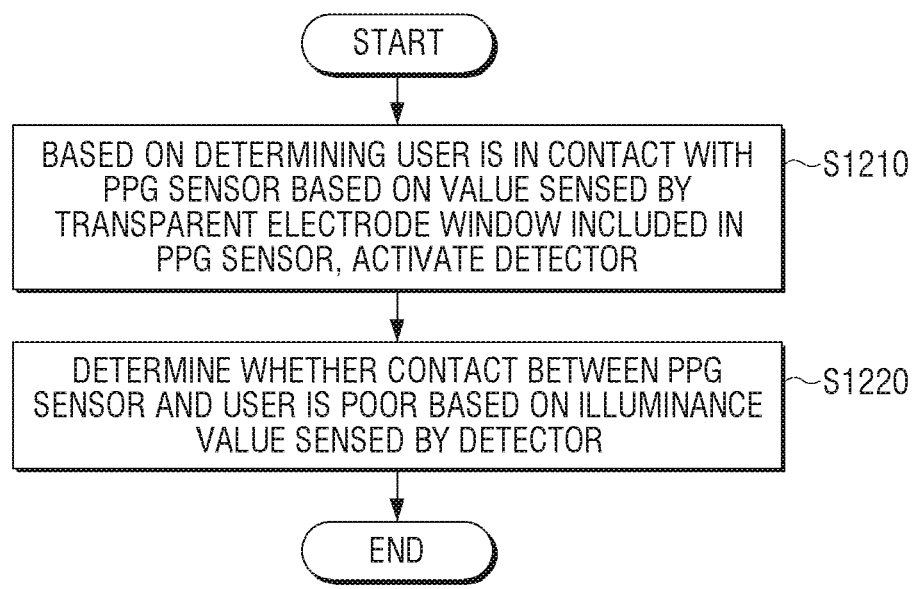
FIG. 12 is a flowchart provided to explain a controlling method of an electronic device according to an embodiment.

FIG. 12 is a flowchart provided to explain a controlling method of an electronic device according to an embodiment.

Referring to FIG. 12, firstly, if it is determined that a user comes in contact with the PPG sensor based on a value sensed by the transparent electrode window included in the PPG sensor, the electronic device may activate the detector (S1210). In this case, activating the detector may mean controlling the detector which has not received light to receive light. In another embodiment, activating the detector may mean controlling the detector which has not processed light even after receiving the light to perform processing the received light and obtain an illuminance value.

Specifically, if the value sensed by the transparent electrode window is within a predetermined range, the electronic device may activate the detector, and if the sensed value is out of the predetermined range, the electronic device may provide a message request the user to touch the PPG sensor. In this case, the value sensed by the transparent electrode window may be at least one of the current value, voltage value, impedance value, or conductivity value.

For example, if the current value sensed by the transparent electrode window is equal to or greater than a predetermined value, the electronic device may activate the detector, and if the sensed current value is less than the predetermined value, the electronic device may provide a message requesting the user to touch the PPG sensor. In this case, the electronic device may display the message on the display or provide the message as a notification through a speaker.

Subsequently, the electronic device may determine whether a contact between the PPG sensor and the user is poor based on the illuminance value sense by the detector (S1220).

Specifically, if the illuminance value sensed by the detector is equal to or greater than a predetermined value, the electronic device may determine that the contact between the PPG sensor and the user is poor. This is because ambient light is sensed as the user's body part does not completely cover the PPG sensor.

In this case, if the illuminance value sensed by the detector is equal to or greater than the predetermined value, the electronic device may provide the user with a message requesting to cover the entire PPG sensor. Here, the electronic device may display the message on the display or provide the message as a notification through a speaker.

Meanwhile, if the illuminance value sensed by the detector is less than the predetermined value, the electronic device may obtain the user's biometric information by activating a light source.

FIG. 13 is a flowchart provided to explain a controlling method of an electronic device according to an embodiment in greater detail.

Referring to FIG. 13, firstly, the electronic device may determine whether an electrode is in contact (S1301). Specifically, the electronic device may determine whether a user is in contact with the transparent electrode window of the PPG sensor. Specifically, the electronic device may determine whether the user is in contact based on the size of at least one of the current value, voltage value, impedance value, or conductivity value which are sensed in the transparent electrode window of the PPG sensor.

In this case, if the user is not contact with the transparent electrode window (S1301-N), the electronic device may keep determining whether the electrode is in contact. Meanwhile, according to an embodiment, if it is required to obtain a bio-signal, when the user's contact is not sensed, the electronic device may provide the user with a message requesting to contact the PPC sensor with a body part. For example, the electronic device may display the message on the display or provide the message as a voice through a speaker.

Meanwhile, if it is determined that the user is in contact with the transparent electrode window (S1301-Y), the electronic device may identify ambient illuminance and measure the illuminance with the detector (S1302). Here, if it is determined that the user is in contact with the transparent electrode window, the electronic device may activate the detector and measure the ambient illuminance. In this case, the electronic device may measure the ambient illuminance using an illuminance sensor which is distinguished from the detector.

The electronic device may obtain an illuminance value using the detector. In this case, the light source of the PPG sensor is in an inactivated state, and the illuminance obtained by the detector may be illuminance by light of the surrounding environment that is not blocked by the user's body part.

In addition, the electronic device may determine whether the illuminance measured by the detector is less than a predetermined value (S1303). Here, the predetermined value is set based on an illuminance value of the surrounding environment, and when the surrounding environment is dark, the predetermined value may be set to a lower value than when the surrounding environment is bright.

In this case, if the illuminance measured by the detector is equal to or greater than the predetermined value (S1303-N), the electronic device may check the cause of the failure to obtain a bio-signal and provide a notification to the user (S1304). Specifically, if the illuminance measured by the detector is equal to or greater than the predetermined value, the electronic device may determine that obtaining a bio-signal is failed because the PPG sensor is not covered sufficiently by the user's body part, and provide a message requesting the user to move the body part so as to cover the PPG sensor sufficiently. Subsequently, the electronic device may determine again whether the user is in contact with the transparent electrode window of the PPG sensor.

Meanwhile, if the illuminance measured by the detector is less than the predetermined value (S1303-Y), the electronic device may initiate measurement of the PPG sensor (S1305). Specifically, the electronic device may obtain the user's bio-signal by activating the light source of the PPG sensor. For example, data may be collected for predetermined initial X seconds required for obtaining a bio-signal.

The electronic device may determine whether a noise of the obtained signal is less than a reference value (S1306). Specifically, the electronic device may determine whether there is a noise by comparing the stored bio-signal of the normal range and the bio-signal obtained by the PPG sensor.

In this case, if the noise is less than the reference value (S1306-Y), the electronic device may determine that the obtained bio-signal is a bio-signal of the normal range, and may continue or complete the measurement. Meanwhile, if the noise is equal to or greater than the reference value (S1306-N), the electronic device may check the cause of failure in obtaining a bio-signal, and provide a notification thereof to the user (S1304). Specifically, if the noise is equal to or greater than the reference value, the electronic device may determine that the user may move during measurement, there is a foreign substance on the surface of the PPG sensor, or too much pressure is applied on the PPG sensor, and provide the user with a message requesting not to move during measurement, to remove the foreign substance on the surface of the sensor, not to press the surface of the sensor strongly, etc. In this case, the electronic device may provide the user with the cause of the signal failure more specifically using a value sensed by an acceleration sensor or a pressure sensor. Subsequently, the electronic device may determine again whether the user is in contact with the transparent electrode window of the PPG sensor.

As described above, by analyzing the characteristics of the transparent electrode window, the detector and the bio-signal, the cause of error in measuring a bio-signal can be identified step by step and provided to the user. Accordingly, it is possible to correct unnecessary waste of power and the cause of measurement failure quickly.

Meanwhile, the diverse embodiments described above may be implemented in a recording medium readable by a computer or a similar device using software, hardware, or a combination of software and hardware. According to a hardware implementation, embodiments described in the disclosure may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, or electric units for performing other functions. In some cases, embodiments described in the specification may be implemented by the processor itself. According to a software implementation, embodiments such as procedures and functions described in the specification may be implemented by separate software modules. Each of the software modules may perform one or more functions and operations described in the specification.

Meanwhile, the methods according to the above-described various embodiments may be stored in a non-transitory readable medium. Such a non-transitory readable medium may be mounted and used in various devices.

The non-transitory computer readable medium is not a medium that stores data for a while, such as a register, a cache, a memory, or the like, but means a medium that semi-permanently stores data and is readable by an apparatus. Specifically, the programs for performing the above-described various methods may be stored and provided in a non-transitory readable medium such as a compact disc (CD), a digital versatile disc (DVD), a hard disc, a Blu-ray disc, a universal serial bus (USB), a memory card, a read only memory (ROM), or the like.

According to an embodiment, the methods according to the various embodiments described above may be provided while being included in a computer program product. A computer program product refers to a product, and it can be traded between a seller and a buyer. The computer program product can be distributed on-line in the form of a storage medium that is readable by machines (e.g.: a compact disc read only memory (CD-ROM)), or through an application store (e.g.: play store™). In the case of on-line distribution, at least a portion of the computer program product may be stored in a storage medium such as the server of the manufacturer, the server of the application store, and the memory of the relay server at least temporarily, or may be generated temporarily.

Although the embodiments of the disclosure have been illustrated and described hereinabove, the disclosure is not limited to the abovementioned specific embodiments, but may be variously modified by those skilled in the art to which the disclosure pertains without departing from the gist of the disclosure as disclosed in the accompanying claims. These modifications should also be understood to fall within the scope and spirit of the disclosure.

What is claimed is:

1. An electronic device comprising:
   a photoplethysmography (PPG) sensor including a light source, a detector, a metal electrode, and a transparent electrode window comprising a transparent electrode; and at least one processor comprising processing circuitry configured to:
   while the light source of the PPG sensor is off,
      based on determining user contact with the PPG sensor based on a value sensed by the transparent electrode, activate the detector;
      receive an illuminance value sensed by the detector;
      based on the illuminance value being equal to or greater than a specified illuminance value, control a display to display a first user interface screen indicating poor user contact with the PPG sensor; and
      based on the illuminance value being less than the specified illuminance value,
         obtain user biometric information from the PPG sensor by activating the light source;
         determine whether a state of PPG sensor interference with a signal corresponding to the biometric information exists; and
         based on determining the state of PPG sensor interference, control the display to display a second user interface screen including information related to the PPG sensor interference.

2. The electronic device as claimed in claim 1, wherein the first user interface screen comprises a message prompting touching of an entire area of the PPG sensor.

3. The electronic device as claimed in claim 1, further comprising:
   memory,
   wherein the at least one processor is configured to:
      obtain a similarity between a first signal obtained by the detector and a second signal of a normal range stored in the memory by comparing characteristics of the first signal obtained by the detector while the light source is activated and characteristics of the second signal; and
      based on the obtained similarity being less than a predetermined similarity value, determine that the state of PPG sensor interference exists.

4. The electronic device as claimed in claim 3, wherein the at least one processor is configured to obtain the similarity by comparing at least one of a frequency, a first differential value or a second differential value of each of the first signal and the second signal.

5. The electronic device as claimed in claim 1, wherein the at least one processor is configured to, based on a value sensed by the transparent electrode being outside a predetermined range, control the display to display a message prompting user touch of the PPG sensor.

6. The electronic device as claimed in claim 1, further comprising:
   an illuminance sensor different from the detector,
   wherein the at least one processor is configured to set the specified illuminance value based on an ambient illuminance value sensed by the illuminance sensor.

7. The electronic device as claimed in claim 1, wherein the transparent electrode window is configured to cover an upper part of the light source and the detector.

8. One or more non-transitory computer-readable storage media storing a program which, when executed by at least one processor of an electronic device comprising a photoplethysmography (PPG) sensor including a light source, a detector, a metal electrode, and a transparent electrode window comprising a transparent electrode, causes the electronic device to perform operations comprising:
   while the light source of the PPG sensor is off,
      based on determining user contact with the PPG sensor based on a value sensed by the transparent electrode, activating the detector;
      receiving an illuminance value sensed by the detector;
      based on the illuminance value being equal to or greater than a specified illuminance value, controlling a display to display a first user interface screen indicating poor user contact with the PPG sensor; and
      based on the illuminance value being less than the specified illuminance value,
         obtaining user biometric information from the PPG sensor by activating the light source;
         determining whether a state of PPG sensor interference with a signal corresponding to the biometric information exists; and
   based on determining the state of PPG sensor interference, controlling the display to display a second user interface screen including information related to the PPG sensor interference.

* * * * *